United States Patent
Brehm et al.

(10) Patent No.: US 7,223,262 B2
(45) Date of Patent: May 29, 2007

(54) CONNECTOR, CONTAINER WITH SUCH A CONNECTOR AND FLUID PREPARATION DEVICE WITH A MATING CONNECTOR FOR SUCH A CONTAINER

(75) Inventors: Winfried Brehm, Hofheim (DE); Thierry Dupin, Bessenay (FR); Ilona Eggert, Schweinfurt (DE); Thomas Faulhaber, Bergrheinfeld (DE); Thomas Graf, St. Jean des Vignes (FR); Philippe Laffay, Sainte Foy les Lyon (FR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 323 days.

(21) Appl. No.: 10/384,732

(22) Filed: Mar. 11, 2003

(65) Prior Publication Data

US 2003/0168120 A1    Sep. 11, 2003

(30) Foreign Application Priority Data

Mar. 11, 2002  (EP)  ................................. 02005510

(51) Int. Cl.
*A61B 19/00* (2006.01)
*A61M 39/00* (2006.01)
*F16L 39/00* (2006.01)
*A61M 37/00* (2006.01)

(52) U.S. Cl. ...................... 604/415; 604/905; 604/533; 604/539; 285/124.1

(58) Field of Classification Search ................ 604/403, 604/408, 415, 416, 905, 326, 533, 534, 538, 604/288.02, 262, 29, 190, 283, 85, 539; 138/111, 138/112, 116, 89; 285/120.1, 124.1–4; 222/485; 383/210.1, 41; 206/363; 239/266

See application file for complete search history.

(56) References Cited

U.S. PATENT DOCUMENTS

| | | | | |
|---|---|---|---|---|
| 3,512,806 A | * | 5/1970 | Fullmer et al. | 285/124.4 |
| 4,048,996 A | * | 9/1977 | Mittleman et al. | 604/86 |
| 4,479,989 A | * | 10/1984 | Mahal | 428/35.5 |
| 4,547,900 A | * | 10/1985 | Larkin et al. | 383/5 |
| 4,786,279 A | | 11/1988 | Wilkinson et al. | 604/88 |
| 4,892,222 A | * | 1/1990 | Schmidt et al. | 215/247 |
| 5,540,265 A | | 7/1996 | Polaschegg et al. | 141/301 |
| 6,460,592 B1 | * | 10/2002 | Sano et al. | 156/503 |
| 6,517,526 B1 | * | 2/2003 | Tamari | 604/403 |
| 6,979,322 B2 | * | 12/2005 | Chu et al. | 604/248 |

FOREIGN PATENT DOCUMENTS

| | | |
|---|---|---|
| DE | 31 35 150 | 1/1983 |
| DE | 32 47 294 | 7/1983 |
| GB | 1156031 | 6/1969 |
| WO | 83/00812 | 3/1983 |

* cited by examiner

*Primary Examiner*—Tatyana Zalukaeva
*Assistant Examiner*—Leslie R. Deak
(74) *Attorney, Agent, or Firm*—Jacobson Holman PLLC

(57) ABSTRACT

The invention relates to the field of connectors for connecting a container with a fluid preparation device for preparing a fluid, in particular a container with a concentrate for the preparation of dialysis fluid. In order to simplify the handling during both the manufacturing process of such containers and the connection of such containers to the fluid preparation devices, the invention proposes a design of a connector (1) for connecting a first and second fluid line of the container with a third and fourth fluid line of the fluid preparation device with two lateraly spaced-apart mounting means (2, 4) which each incorporate one of two orifices (3, 5) terminating the first and second fluid lines. The invention also concerns a corresponding container and fluid preparation device.

22 Claims, 6 Drawing Sheets

CONNECTOR, CONTAINER WITH SUCH A CONNECTOR AND FLUID PREPARATION DEVICE WITH A MATING CONNECTOR FOR SUCH A CONTAINER

BACKGROUND OF THE INVENTION

1. Field of the Invention

The invention relates to the field of connectors for connecting a container with a fluid preparation device for preparing a fluid. The invention also relates to such containers and fluid preparation devices, in particular to dialysis devices.

2. Description of the Related Art

Most hemodialysis devices used for routine treatment prepare the required dialysis fluid themselves by a fluid preparation part which is contained in the device and where the mixing of adequate concentrates with water takes place. These concentrates are commonly distributed in liquid form and filled in canisters. Both the handling and transportation of such canisters filled with fluid concentrates pose various problems. Special and rather spatial connectors are necessary on the dialysis device to couple such canisters so that the device can suck the required concentrate. During exchange of a canister, fluid can be spilled. Special chambers for accommodating or even rinsing the connector during any periods when no canister is connected may be required. As far as the weight is concerned, it is primarily only water which is delivered from the manufacturer to the patient. Furthermore, the empty canisters represent an environmental problem as only special material with certain blocking and stability properties should be used.

It is also known to provide concentrates, for instance in a clinic, from a central preparation unit to various treatment sites by an installed piping network. Though this simplifies the working load at the treatment sites in these clinics it is obvious that such a piping network is expensive, both for installation and maintenance, and not applicable for more flexible conditions.

It is also known to use at least for some ingredients of the dialysis fluid a powdered or granulated solid concentrate such as bicarbonate. U.S. Pat. No. 5,540,265 describes such a system with a bag containing a concentrate and having a plug component. On the dialysis device there is a complementary plug component by which a flow connection for a first and a second flow path with the interior of the bag may be established. Water is introduced into the bag by the first flow path. Diluted and thus prepared bicarbonate fluid is extracted by the second flow path.

The plug component has a coaxial design for the two flow paths. The complementary plug component on the dialysis device therefore has a rather sophisticated design which in turn requires elaborate solutions to make routine rinsing and disinfection of this part of the dialysis device possible. Furthermore, as the plug component on the bag has a circular design the manufacturing process of such a bag affords special processes as the plug component is usually welded into a complementary hole in a side wall of the bag. More simple techniques assessing the bag only from the top are hence not applicable.

SUMMARY OF THE INVENTION

It is therefore an object of the invention to provide a connector for a container to be coupled to a mating connector on a fluid preparation device such as a dialysis device which considerably simplifies the handling during the connection procedure, the manufacturing process of the container and the rinsing and disinfection of the mating connector part on the fluid preparation device.

It is also an object of the invention to provide a corresponding container. Furthermore, it is an object of the invention to provide a fluid preparation device with a corresponding mating connector.

These objects of the invention are solved by a connector for connecting fluid lines with a first connector part providing a first orifice for connecting a first fluid line to a third fluid line, a second connector part providing a second orifice for connecting a second fluid line to a fourth fluid line, and a mounting means enabling the connection of the first and second connector parts to mating parts of a mating connector. The mounting means comprises two laterally spaced-apart mounting means enabling connection to two equally laterally spaced-apart mounting means of the mating connector, with each of the two mounting means incorporating one of the two orifices. The present invention further includes the combination of a connector as just described with a container having a containment portion.

The objects of the invention are also solved by a fluid preparation device including a source for a flushing fluid which is connected to a flushing fluid line, a prepared fluid line for fluid to be prepared, a container having an interior filled with a fluid medium, a mounting connector part having first and second mating mounting means suitable for mounting and connecting the container such that the flushing fluid line and the prepared fluid line are in fluid communication with the interior of the container, and a connector. The connector has a first connector part providing a first orifice for connecting a first fluid line to the flushing fluid line, a second connector part providing a second orifice for connecting a second fluid line to the prepared fluid line, and two laterally spaced-apart mounting means for connecting the first and second connector parts to the mounting connector part, with each of the two mounting means incorporating one of the first and second orifices.

The concept of the invention is based on the observation that by separating the mounting means which comprises both fluid line connector parts for the two fluid lines to be connected to two fluid lines of the fluid preparation device, into two laterally spaced-apart mounting means, each incorporating the orifices of one of the two connector parts, it is possible to set up a connector system which significantly simplifies the handling and manufacturing processes. With the aid of the inventive concept it is in particular possible to design a container to be connected to a fluid preparation device, which is mounted in a suspended fashion with the connector parts being used at the same time in a hook-like fashion at the uppermost point of the container to realize an optimum stability of the mounted container.

BRIEF DESCRIPTION OF THE DRAWINGS

These and other advantages of the invention will become more apparent from an embodiment which is now described as an example by the aid of the drawings. In the drawings.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
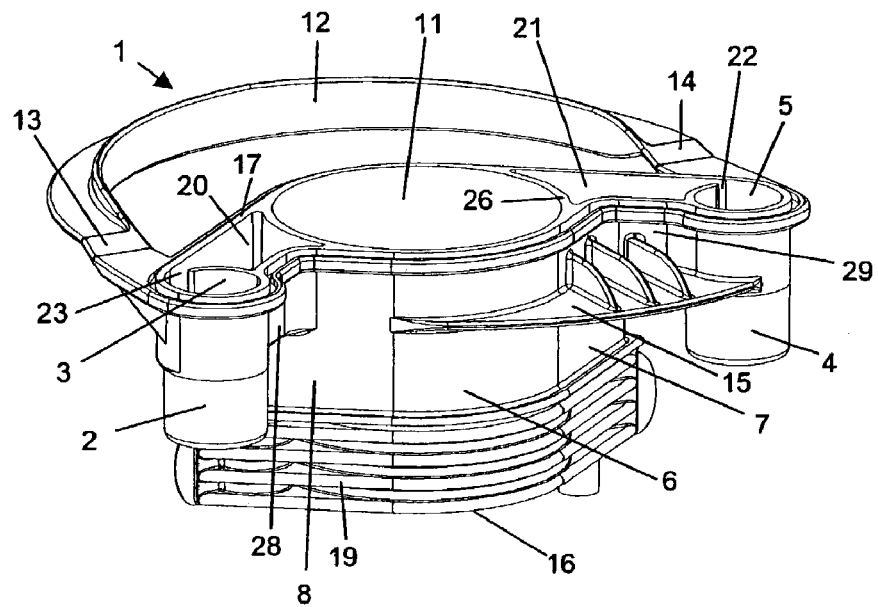
FIG. 1 shows a perspective view of an embodiment of the connector according to the invention with a boat-like cross-section.

In FIG. 1 an embodiment of a connector according to the invention is shown in a perspective view. The connector 1 has two bar-like, laterally spaced-apart connecting parts or mounting means 2 and 4. Such mounting means may easily be mounted to a mating mounting means by insertion in an axial direction. The interior of the mounting means 2 an 4 is hollow thus defining first and second orifices 3 and 5.

The connector 1 has a boat-like cross-section with a wide middle part 6 and two wing-like projections 7 and 8 on opposing sides of the middle part 6. The boat-like cross-section simplifies the joining of the connector to a containment portion of a container like a flexible tube bag considerably, as is known in the art of manufacturing flexible bags. For welding purposes there may therefore be provided a rip structure 19 at the lower end 16 of the connector 1.

The middle part 6 of the boat-like cross-section shows a fifth orifice 11 which extends from the upper end 17 to the lower end 16. The orifice 11 may be used for prefilling the containment portion to be joined to the connector during the manufacturing process with a substance.

The mounting means 2 and 4 protrude from the wing-like projections 7 and 8 by protrusions 28 and 29 in a direction which is perpendicular to the axes of the mounting means 2 and 4 and thus also to the axes of the orifices 3, 5 and 11, which are all parallel. In the embodiment shown in FIG. 1, the protrusions 28 and 29 are tangential to one side of the wing-like projections 7 and 8.

Furthermore, a first end 13 of a handle 12 is joined to the first mounting means 2 and a second end 14 of the handle 12 is joined to the second mounting means 4. To ease the use of the handle 12 the ends 13 and 14 may comprise flexible film joints.

The connector 1 also comprises a ledge 15 which joins the second mounting means 4 with the middle part 6 of the connector 1. This ledge 15, as will be outlined below, serves as a counterpart for a detector means at the mating connectors site for confirming the correct mount of the connector.

Figure 2:
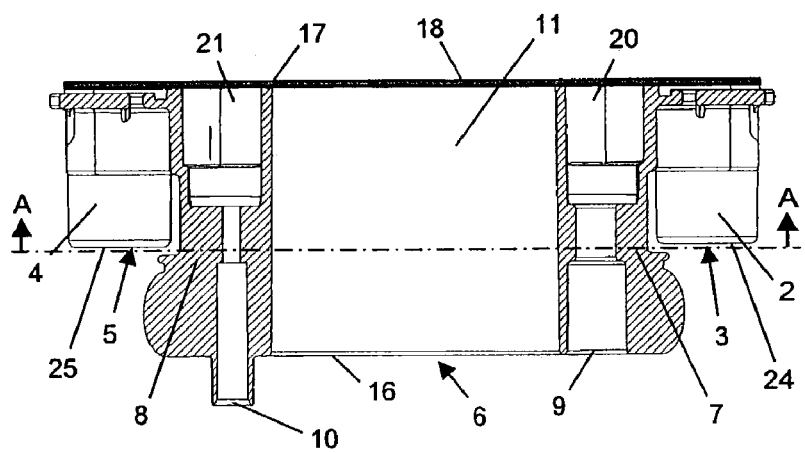
FIG. 2 shows a first sectional drawing of the connector shown in FIG. 1.

In FIG. 2 a sectional view of the container 1 is shown where the middle part 6 and the wing-like projections 7 and 8 are cut along their middle, and the view is from the back as seen in FIG. 1. The connector 1 extends from the lower end 16 to the upper end 17. In the middle part the continuous orifice 11 for enabling an easy prefilling of the containment portion to be joined to the lower end 16 of the container is seen.

In the first wing-like projection 7 there is also a continuous third orifice 9 and in the second wing-like projection 8 a continuous fourth orifice 10. Though the third and fourth orifice 9 and 10 have a varying cross-section along their extensions from the lower end 16 to the upper 17 of the container 1, this has no influence on the fact that a fluid communication is established along these extensions. The third orifice 9 extents to a first distribution chamber 20 and the fourth orifice 10 to a second distribution chamber 21.

As can be seen in FIG. 1 the distribution chambers 20 and 21 are in fluid communication with the first and second orifices 3 and 5 by slots 22 and 23, respectively. By mounting the connector 1 in a mating mounting means to be described below, fluid communication is thus established from the first orifice 3 to the third orifice 9 which hence constitutes a first fluid line, and from the second orifice 5 to the fourth orifice 10 which constitutes a second fluid line.

Figure 3:
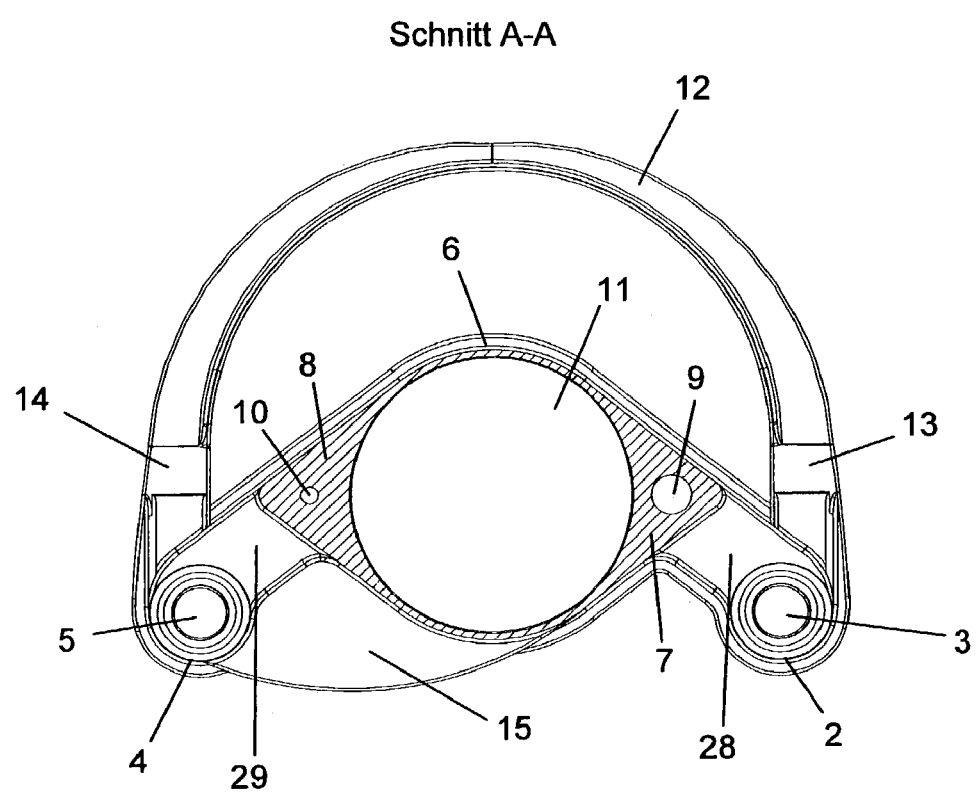
FIG. 3 shows a second sectional drawing as defined by FIG. 2.

FIG. 3 shows a further sectional view along the line A—A as indicated in FIG. 2. In this view the protrusions 28 and 29 of the two mounting means 2 and 4 and thus the first and second orifices 3 and 5 in a direction perpendicular to the vertical extension of the wing-like projections 7 and 8 and the middle part 6 of the connector 1 are displayed more clearly.

In an embodiment of a container according to the invention the connector 1 shown in FIGS. 1 to 3 is representing the connector portion, the lower end 16 to be joined to a containment portion of the container. For this purpose the upper end 17 is sealed along the circumference 26—which is also encircling and thus sealing the fifth orifice 11—by a flexible sheet 18 by welding or similiar known joining techniques. It is worth noting that due to the design of the connector the flow paths for the first and second fluid lines are not blocked by this seal. The flexible sheet 18 is indicated in FIG. 2.

Figure 4:
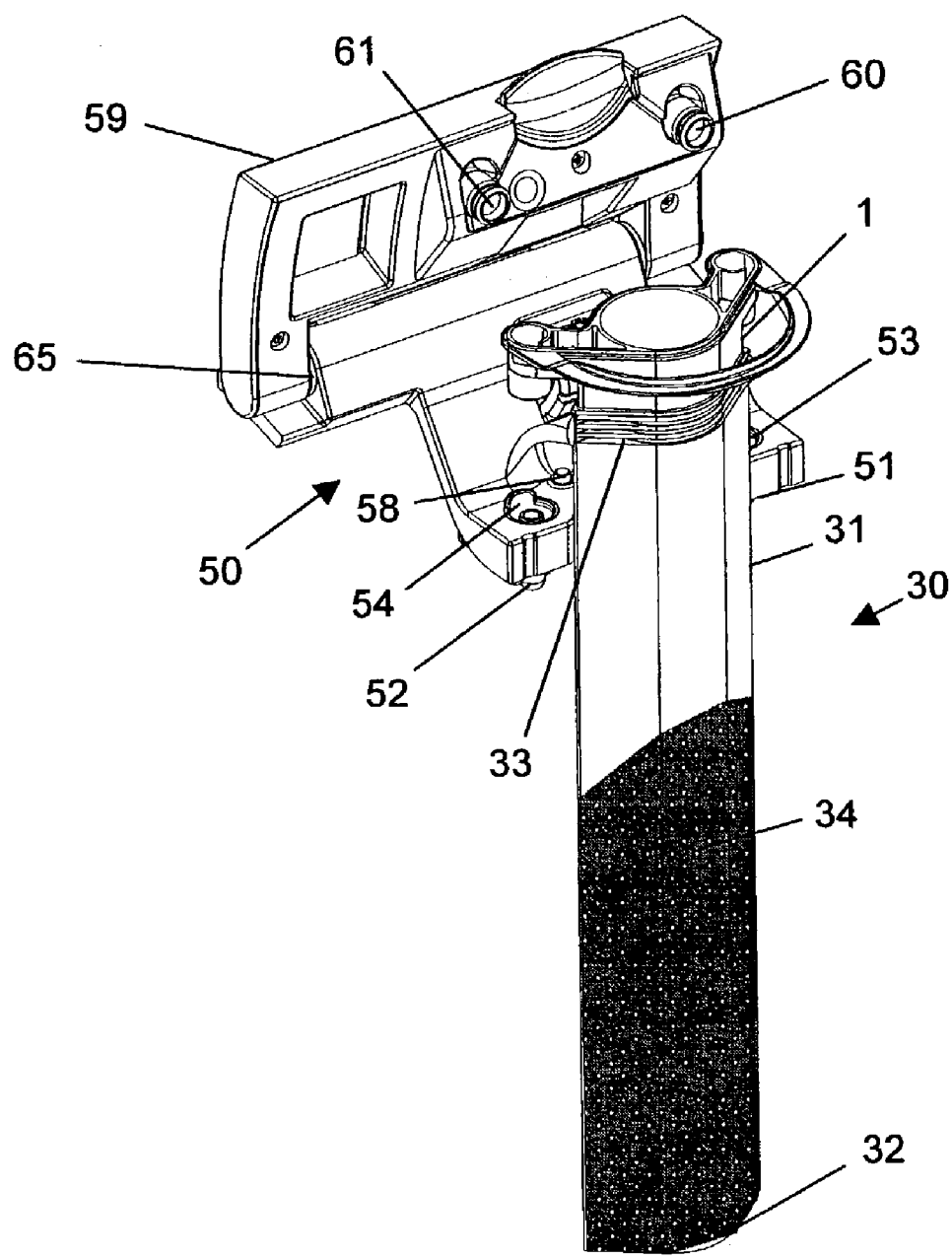
FIG. 4 shows an embodiment for a container according to the invention using the connector shown in FIGS. 1 to 3, and a part of an embodiment of the fluid preparation device according to the invention, which is suitable for mounting the container, a lid of that part being in a first position.

This embodiment of the container is shown in FIG. 4. The containment portion 31 of the container 30 is made from a tube bag which is sealed at the lower end 32 and joined by welding or similar techniques in a leak-proof manner at the upper end 33 to the lower end 16 of the connector 1. In the embodiment shown in FIG. 4 the container 30 is furthermore prefilled with a powdered concentrate 34 of a substance to be dissolved for final usage. The substance may be provided in any other condition, solid or fluid, whatever may be useful for the particular purpose.

Figure 8:
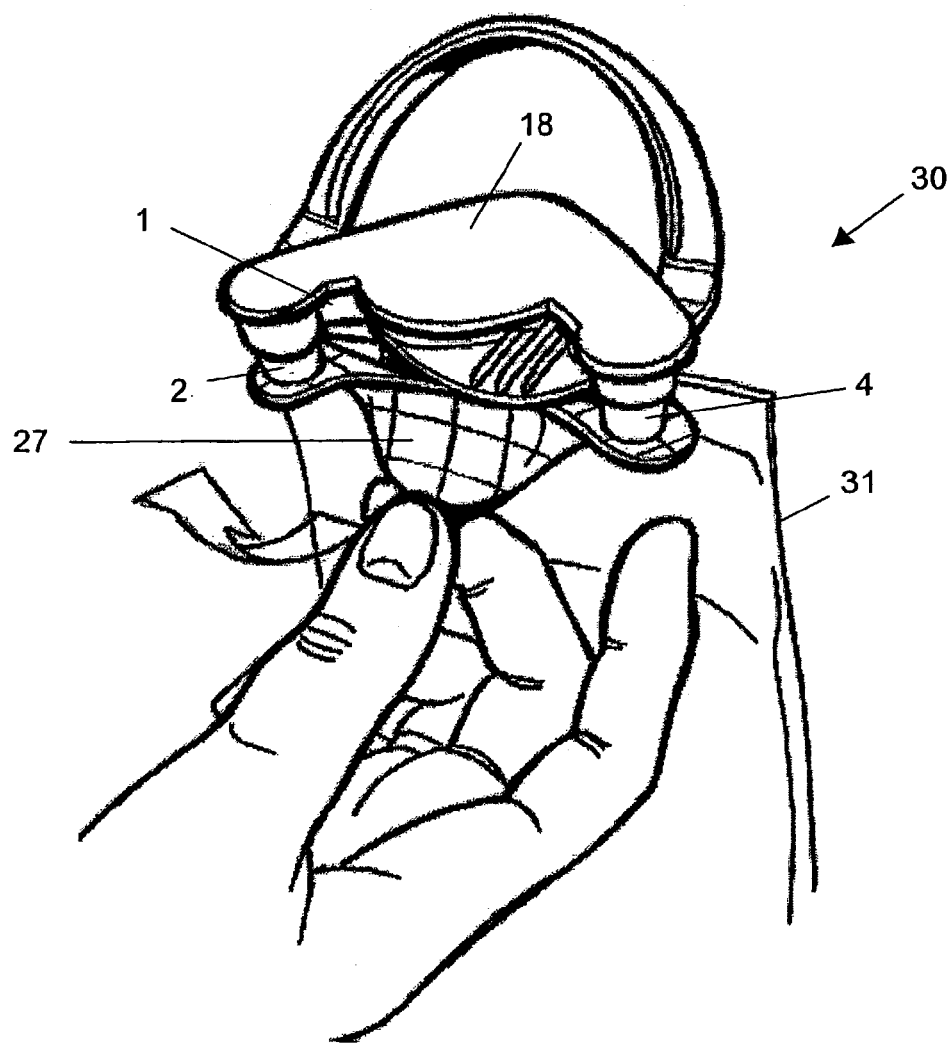
FIG. 8 shows removal of a flap-like seal from the container prior to use thereof.

For maintaining sterility before usage the lower ends 24 and 25 of the orifices 3 and 5 may be sealed in an appropriate way so that the interior of the container 30 is completely sealed to the exterior. As an example a single flap-like seal 27 is shown in FIG. 8 which is sealing both orifices 3 and 5. The seal 27 may be removed by a user before usage by peeling off the seal as shown in FIG. 8.

Furthermore, not shown tubes and/or filters may be provided in the container 30 which are placed in the first and/or second fluid line in order to filter passing fluid flowing in and/or out the bag and/or extend the lines to a particular site within the containment portion 31. If it is desired to withdraw a saturated solution of a substance to be dissolved it may prove useful to introduce the flushing and hence dissolving fluid like water close to the upper end 33 of the containment portion 31 and to withdraw the saturated solution close to the lower end 32 of the containment portion 30.

In FIG. 4 there is also shown a part 50 of an embodiment for a fluid preparation device according to the invention which has mating first and second mounting means 53 and 54 for mounting the connector 1 and thus container 30. These mating first and second mounting means are formed by first and second insertion chambers 53 and 54 which have a complementary cross-section such that the first and second bar-like mounting means 2 and 4 can be mounted by insertion into these chambers. Any cross-section may be used, but a circular cross-section as shown in this embodiment is advantageous in view of improved rinsing and disinfection properties.

The first insertion chamber 53 is in fluid communication with a third fluid line 51, the flushing fluid line, which is connected to a flushing fluid source (not shown) for the delivery of flushing fluid. This flushing fluid is required during use of the container 30 in order to prepare the prepared fluid from the prefilled substance and the flushing fluid—the latter being in most cases simply water. Correspondingly the second insertion chamber 54 is in fluid communication with a fourth fluid line 52, the prepared fluid line, which enables the delivery of the prepared fluid to a place where it is required. This may still be within the fluid preparation device or by means of a suitable outlet for the delivery to somewhere else.

The part 50 of the fluid preparation device also comprises a detector means 58 which in this embodiment is a mechanical microswitch. Upon mounting the container 30 and thus the connector 1, the ledge 15 presses the switch 58 which by a not shown electronic evaluation circuit of the fluid preparation device enables the device to confirm the correct mount of the connector 1. It may be possible that this evaluation circuit causes any actuators to block the flow of any flushing fluid into the first insertion chamber 53 until such confirmation has taken place.

The part 50 of the fluid preparation device further comprises a lid 59. The lid 59 is turnable around a joint 65 from a first, open position which is shown in FIG. 4, to a third, closed and preferable locked position which will be described below. Between the first and the third position, the lid is arrestable, preferably lockable, in a second position with the container 30 being mounted as will also be explained below. The lid 59 has first and second closure parts 60 and 61 which are suitable to close the first and second insertion chambers 53 and 54, respectively, when the lid 59 is in the third position.

Figure 5:
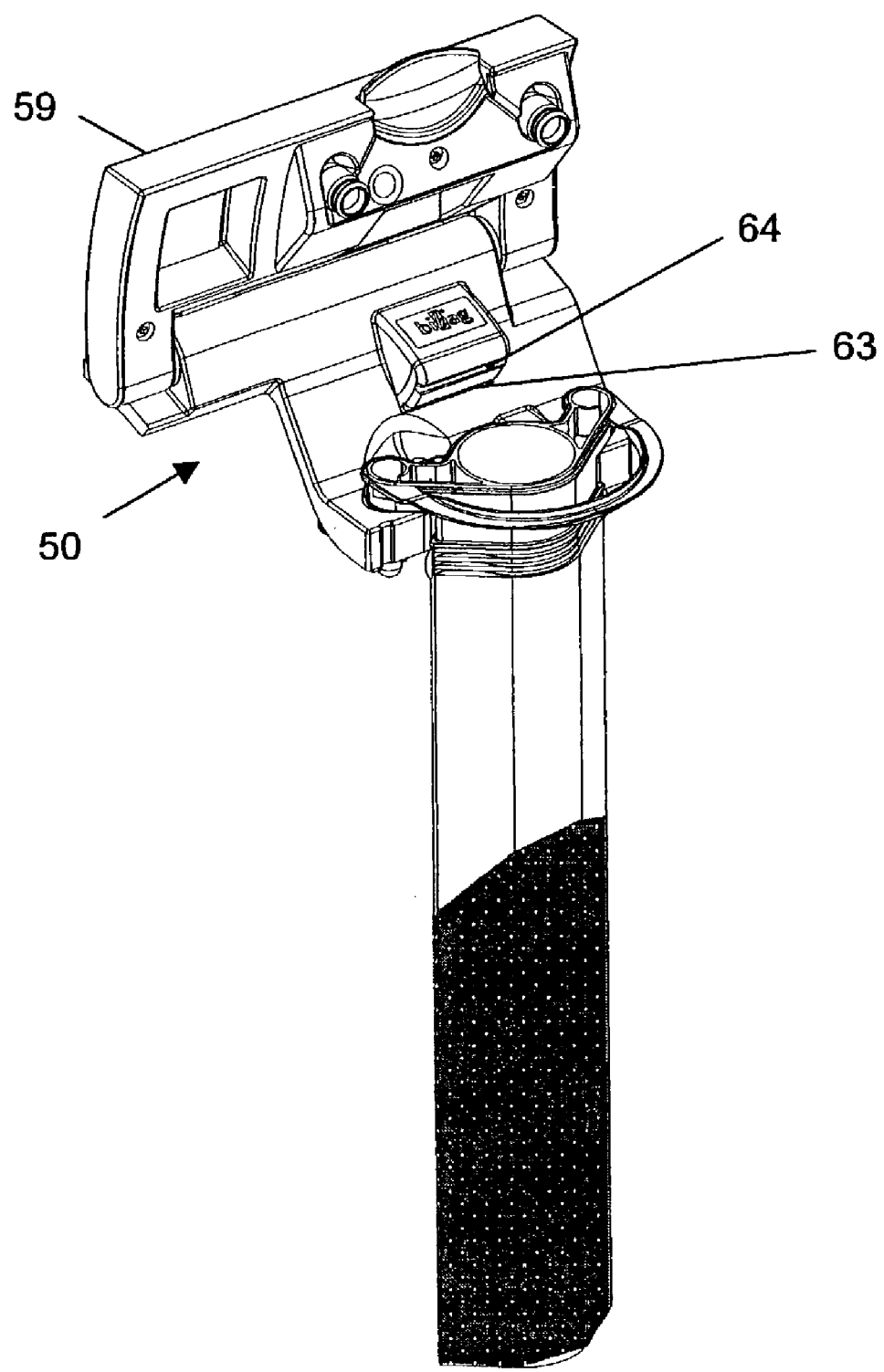
FIG. 5 shows the same arrangement as FIG. 4, the container being mounted.

FIG. 5 shows the same view as FIG. 4 with the connector 1 and thus the container 30 being mounted to the part 50 of the fluid preparation device. The first and second mounting means 2 and 4 are inserted in the first and second insertion chambers 53 and 54. Furthermore, there are two proximity detectors 63 and 64 on the part 50 which detect the presence of the lid 59 in either the second or the third position. These proximity sensors may be non-mechanical sensors like Hall sensors which notice the close position of certain parts of the lid 59. These sensors may as well comprise mechanical switching means which are actuated by movable counterparts (not shown) of the lid which at the time serve to lock the lid 59 in the second or third position.

Figure 6:
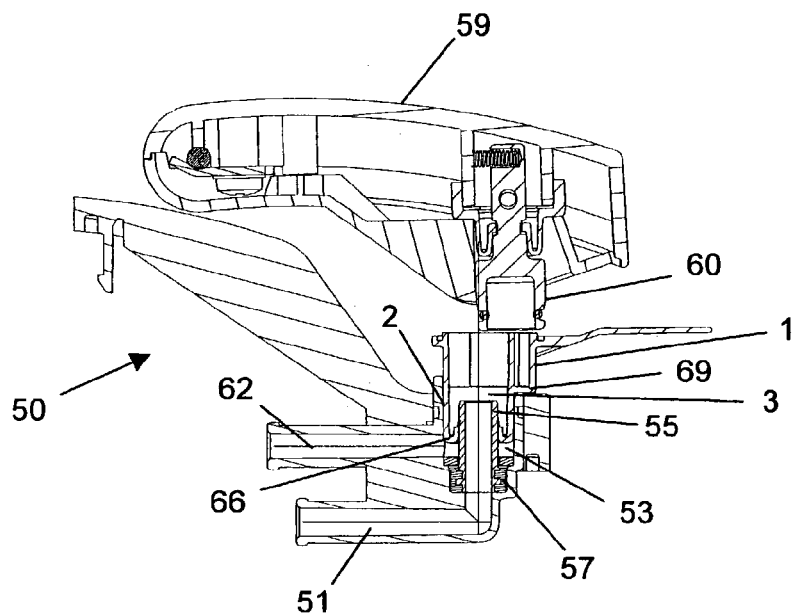
FIG. 6 shows a first sectional view of that part of the fluid preparation device with the container being mounted, the lid being in a second position.

FIG. 6 shows a first sectional view of the arrangement shown in FIG. 5 with the lid 59 being in the second position, arresting the connector 1 in its mounted position by pushing with the closure parts 60 and 61 onto the connector 1. The sectional view is taken along the flushing fluid line 51 and the first insertion chamber 53 looking from left to right in FIG. 5. The prepared fluid line 52 and the second insertion chamber 54 have a symmetric design.

Within the first insertion chamber 53 there is first male connector element 55 which terminates the flushing fluid line 51 within the first insertion chamber 53. The first male connector element 55 is joined to the housing of part 50 with a flexible sealing and compensation element 57 which may be made of any suitable material, e.g. rubber. The sealing and compensation element 57 enables movements of the first male connector element 55 relative to the housing in order to compensate tolerances which may exist for the relevant counterparts of the connector 1.

In the arrangement displayed in FIG. 6 the first orifice 3 and hence the first fluid line of the connector 1 and container 30 are now in fluid communication with the flushing fluid line 51. The orifice 3 is limited by first sealing lips 66 at the lower circumference of the first mounting means 2. The sealing lips 66 may easily be created by injection molding. The lips 66 assure a leak-proofed connection to the first male connector element 55 which they encompass at its outer circumference.

The first mounting means 2 is inserted into the first insertion chamber 53 until a first steplike projection 69 of the first mounting means 2 is touching the housing of the part 50 of the fluid preparation device.

From the first insertion chamber 53 there also branches off a fifth fluid line 62. When the connector 1 is mounted this fifth fluid line 62 will be sealed by the first sealing lips 66, i.e. there is no fluid communication to the connected first and third fluid lines, that latter being the flushing fluid line 51.

For the connection of the second and fourth fluid lines there are corresponding elements, i.e. a second male connector element, a second sealing and compensation element, second sealing lips, a second step-like projection and a branching sixth fluid line.

Figure 7:
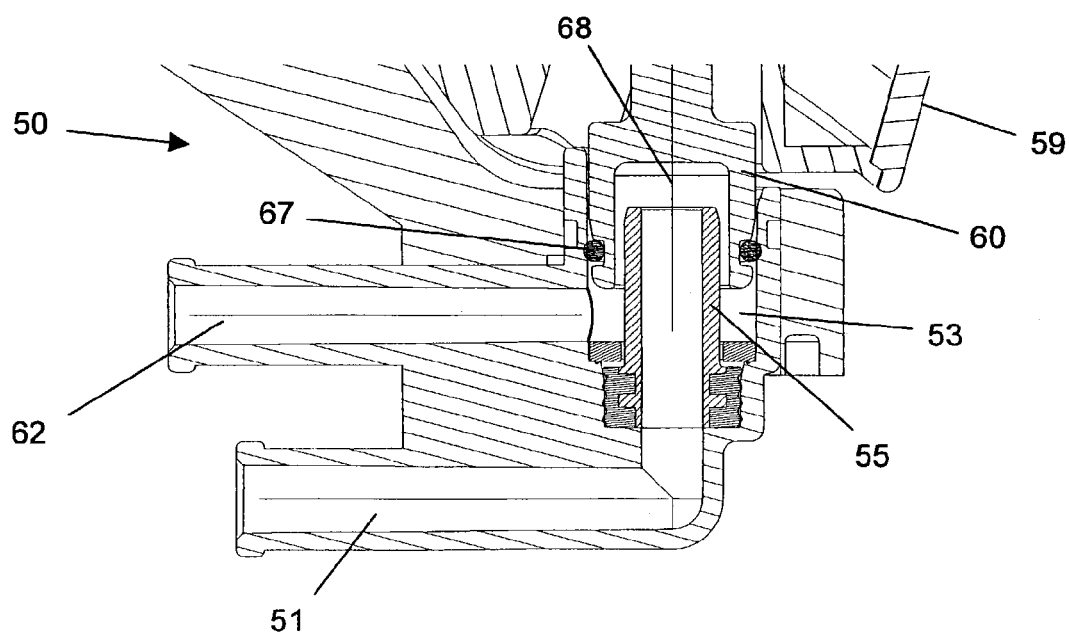
FIG. 7 shows a second sectional view of that part of the fluid preparation device without the container being mounted, the lid being in a third position.

The purpose of the fifth and sixth fluid lines becomes apparent from FIG. 7. This figure shows a second sectional view of the part 50 of the fluid preparation device. It differs from FIG. 6 by the fact that no connector 1 is mounted and that the lid 59 is in the closed, third position. The first insertion chamber 53 is now closed by the first closure part 60 which is a part of the lid 59. The closure is sealed by sealing means 67 on the outer circumference of the first closure part 60, which here is accomplished by an O-ring gasket. On the inner side of the first closure part 60 there is a first opening 68 which has a larger diameter than the outer diameter of the first male connector element 55.

In this configuration the fluid lines of the part 50 of the fluid preparation device may easily be rinsed with any fluid like water or disinfection fluid. As the second closure part 61 is sealing the second insertion chamber 54 in a similar way, the rinsing fluid may be provided by the third fluid line, i.e. the flushing fluid line 51. The flushing fluid then enters the first insertion chamber 53 and leaves it via the fifth line 62. In this embodiment the fifth and sixth lines are joined (not shown). The rinsing fluid hence enters the second insertion chamber 54 by the sixth fluid line and leaves it by the fourth fluid line, i.e. the prepared fluid line 52. By this configuration an easy and effective rinsing and/or disinfection of all relevant parts of the fluid preparation device in the mating connector area is accomplished. Any parts which are above the gasket 67 are not reached by the rinsing fluid, but these parts will not be part of the fluid path if a connector 1 is connected either.

The connector 1 or container 30, respectively, may be designed as a disposable article for single-use purposes. Hence special solutions for their disinfection have not to be found. In this case a sensitive part like the sealing lips 66 is automatically exhanged from one use to another without affording any extra parts or expensive maintenance procedures.

The detector means 63 and 64 sense the lid 59 in the second or the third position. The electronic evaluation circuitry of the fluid preparation device is monitoring the signals provided by these detector means in order to confirm an expected position of the lid 59 during specific modes of the fluid preparation device like disinfection or online fluid preparation.

It is worth noting that the boat-like cross section of the connector 1 represents a preferred embodiment. Any other shape of the connector which still meets the concept of the invention as outlined by the claims would nevertheless enable an easy handling of the connector system during use. As is apparent from FIGS. 4 to 7 the shape of this part of the connector hardly has any influence on the connection steps themselves.

The invention is hence providing easy to handle and reliable components for a fluid preparation system consisting of a container with a special connector and a fluid preparation device. The container may be prefilled with a substance, but also applications are possible where an initially empty container is used which will be filled and/or emptied during use. The container can be of any type, rigid or flexible. A flexible bag represents however a preferred embodiment.

The components of the inventive system are particularly useful in the medical field where the handling is especially sensitive to sterility conditions. At the same time the invention provides inexpensive solutions which is not of lesser interest. The invention has proven particularly useful in the field of dialysis where the fluid preparation device is part of the dialysis device. The prepared fluid may represent only a part of the complete dialysis fluid like bicarbonate, or the complete dialysis fluid. It may be applied to any type of dialysis like hemodialysis or peritoneal dialysis.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A connector for connecting fluid lines comprising:
a connector body having a boat-like cross-section with a wide middle section and first and second wing-like projections on opposite sides of the middle section;
a first connector part protruding from said first wing-like projection and having a first orifice configured to connect a first fluid line to a third fluid line;
a second connector part protruding from said second wing-like projection and having a second orifice configured to connect a second fluid line to a fourth fluid line, said first orifice and said second orifice having parallel axes that are generally vertical when said connector is in use and said first and second connector parts respectively protruding outwardly from said first and second wing-like projections in a direction generally perpendicular to said parallel axes; and
said first and second connector parts being laterally spaced-apart for enabling connection of said connector to two equally laterally spaced-apart mounting parts of a mating connector structure.

2. The connector according to claim 1, further comprising a third orifice in the first wing-like projection and a fourth orifice in the second wing-like projection, said third orifice being in fluid communication with said first orifice, and said fourth orifice being in fluid communication with said second orifice.

3. The connector according to claim 2, further comprising a fifth orifice in said middle section.

4. The connector according to claim 1, further comprising a handle with two ends, each of said ends being joined to a respective one of said two connector parts.

5. The connector according to claim 1, further comprising a ledge joining the middle section and one of said two connector parts.

6. The combination of a connector and a container having a containment portion, said connector comprising:
a connector body having a boat-like cross-section with a wide middle section and first and second wing-like projections on opposite sides of the middle section;
a first connector part protruding from said first wing-like projection and having a first orifice configured to connect a first fluid line to a third fluid line;
a second connector part protruding from said second wing-like projection and having a second orifice configured to connect a second fluid line to a fourth fluid line, said first orifice and said second orifice having parallel axes that are generally vertical when said connector is in use and said first and second connector parts respectively protruding outwardly from said first and second wing-like projections in a direction generally perpendicular to said parallel axes; and
said first and second connector parts being laterally spaced-apart for enabling connection of said connector to two equally laterally spaced-apart mounting parts of a mating connector structure; and
said container coupled to said connector body.

7. The combination according to claim 6, wherein said containment portion includes a bag for containing a dry or fluid medium.

8. The combination according to claim 7, wherein said bag contains an ingredient of a dialysis fluid.

9. The combination according to claim 8, wherein said ingredient is a concentrate of said dialysis fluid.

10. The combination according to claim 7, wherein said bag is a tube bag with one end being sealed and the other end being closed by the connector.

11. The combination according to claim 6, wherein a lower end of the connector is sealed to atmosphere by said containment portion, an upper end of the connector is sealed to the atmosphere by a first seal, and said first and second orifices are sealed to the atmosphere by a second seal.

12. A fluid preparation device for use with a container comprising:
a flushing fluid line for a flushing fluid;
a prepared fluid line for fluid to be prepared;
a mounting connector structure with first and second mating mounting parts having a fixed lateral spacing and having first and second insertion chambers suitable for mounting and connecting a combination of a connector and a container such that, when the combination is mounted, said flushing fluid line and said prepared fluid line are in fluid communication with an interior of the container, and such that the connector has a first connector part having a first orifice for connecting a first fluid line to said flushing fluid line, and a second connector part having a second orifice for connecting a second fluid line to said prepared fluid line, said first orifice and said second orifice having parallel axes that are generally vertical when said connector is in use, said first and second connector parts being laterally spaced-apart at a fixed distance corresponding to said fixed lateral spacing of said first and second mating mounting parts of said mounting connector structure for connection thereto by insertion of said first and second connector parts into said first and second insertion chambers, respectively, each of said first and second connector parts protruding outwardly from the connector body by protrusions in a direction generally perpendicular to said two parallel axes of said two orifices; and a first male connector element terminating said flushing fluid line and a second male connector element terminating said prepared fluid line.

13. The fluid preparation device according to claim 12, further comprising a sealing and compensation element inserted into each of the first and second insertion chambers to seal and compensate for movement of said first and second male connector elements.

14. The fluid preparation device according to claim 12, wherein said first and second insertion chambers have orientations that are substantially parallel with one another.

15. The fluid preparation device according to claim 12, further comprising a detector element for detecting a presence of said connector.

16. The fluid preparation device according to claim 12, further comprising a lid for covering said mounting connector structure.

17. The fluid preparation device according to claim 16, wherein said lid includes a first closure part for closing the first insertion chamber and a second closure part for closing the second insertion chamber.

18. The fluid preparation device according to claim 17, further comprising a fifth fluid line being in fluid communication with the first insertion chamber and thus the flushing fluid line when the first closure part closes the first insertion chamber, and a sixth fluid line being in fluid communication with the prepared fluid line when the second closure part closes the second insertion chamber.

19. The fluid preparation device according to claim 18, wherein said fifth and sixth fluid lines are joined.

20. The fluid preparation device according to claim 16, wherein said lid is movable between a first position enabling the connector to be mounted and/or removed, a second position in which the lid keeps a mounted connector in place, and a third position in which the first and second insertion chambers are closed and no connector is mounted.

21. The fluid preparation device according to claim 20, further comprising a lid position detector component for detecting at least one of said first, second and third lid positions.

22. The fluid preparation device according to claim 12, wherein said connector has a middle section and two wing-like projections arranged laterally on opposite sides of said middle section and extending outwardly therefrom, said first and second connector parts protruding from said wing-like projections, respectively, in a direction generally perpendicular to said parallel axes of said orifices.

* * * * *